United States Patent
Stocking et al.

(10) Patent No.: US 6,726,659 B1
(45) Date of Patent: Apr. 27, 2004

(54) CATHETER ASSEMBLY HAVING A FENESTRATED DILATOR

(76) Inventors: John E. Stocking, 9905 Winged Fort Dr., Louisville, KY (US) 40223; Francis Duque, 7810 Wolf Creek Ct., Louisville, KY (US) 40241

(*) Notice: Subject to any disclaimer, the term of this patent is extended or adjusted under 35 U.S.C. 154(b) by 0 days.

(21) Appl. No.: 09/457,661

(22) Filed: Dec. 9, 1999

(51) Int. Cl.[7] ............................................. A61M 5/178
(52) U.S. Cl. ........................... 604/164.09; 604/164.01; 604/264
(58) Field of Search ................. 604/506–508, 604/510, 513, 158–163, 164.01, 164.02, 164.04, 164.05, 164.07, 164.09, 164.11, 164.12, 167.01, 167.02, 167.03, 167.05, 168.01, 171, 256, 264

(56) References Cited

U.S. PATENT DOCUMENTS

| | | | |
|---|---|---|---|
| 4,850,975 A | | 7/1989 | Furukawa |
| 4,955,890 A | * | 9/1990 | Yamamoto et al. ......... 604/175 |
| 5,242,410 A | * | 9/1993 | Melker .................... 604/164.1 |
| 5,250,038 A | * | 10/1993 | Melker et al. ......... 604/167.01 |
| 5,328,480 A | | 7/1994 | Melker et al. |
| 5,380,290 A | | 1/1995 | Makower et al. |
| 5,704,914 A | * | 1/1998 | Stocking et al. ....... 604/164.07 |
| 5,827,202 A | | 10/1998 | Miraki et al. |
| 5,833,662 A | | 11/1998 | Stevens |
| 5,904,657 A | * | 5/1999 | Unsworth et al. .......... 600/434 |

* cited by examiner

*Primary Examiner*—Brian L. Casler
*Assistant Examiner*—Michael M. Thompson
(74) *Attorney, Agent, or Firm*—Maurice L. Miller, Jr.

(57) ABSTRACT

An improved catheter assembly featuring a hollow introducer needle, a hollow, flexible dilator containing at least one fenestration through a sidewall thereof, the dilator being slidably disposed over the needle, and a sheath slidably disposed over the dilator. A passageway is formed in the assembly to either show a rapid blood flashback along a lengthwise portion of the assembly or to conduct blood or other biological liquid from the patient to a sideport on the sheath for connection to blood pressure monitoring equipment, infusion/blood sampling equipment, or both, without the necessity of altering connections on or with the assembly after insertion of the needle into the patient.

17 Claims, 4 Drawing Sheets

CATHETER ASSEMBLY HAVING A FENESTRATED DILATOR

FIELD OF THE INVENTION

This invention relates to a catheter assembly which includes a hollow introducer needle, a flexible, fenestrated dilator slidably mounted over the needle, a flexible sheath slidably mounted over the dilator and means for viewing an early occurring blood or other biological liquid flashback, indicative of proper placement of the needle and/or dilator in a biological organism. The invention also relates to such an assembly wherein provision is made for monitoring blood pressure, sampling blood and for liquid infusion as soon as the needle penetrates a blood vessel prior to placement of the dilator and sheath therein without the necessity of changing connections to the assembly.

BACKGROUND OF THE INVENTION

Broadly speaking, catheter assemblies having a hollow introducer needle, a flexible dilator slidably mounted over the needle and a sheath slidably mounted over the dilator for successive insertion into a blood vessel or other biological liquid containing region of a human or animal body have long been known and used in the prior art. A difficulty that has been encountered with all known prior art catheter assemblies of this type is that, in order to use blood pressure monitoring equipment to determine with a high degree of certainty whether the needle has been properly inserted into a vein, as opposed to an artery, or vice versa, prior to placement of the dilator and sheath into the blood vessel, certain elements of the assembly must first be disconnected in order to connect blood pressure monitoring equipment. Such changing of connections on the assembly is time consuming and is often an awkward process. Yet such a process is essential in order to determine with certainty the proper placement of the needle prior to placement of the dilator and sheath.

The difficulty exists because of the lack of any provision for communication of blood from the vessel penetrated by the needle with a cavity within a hub of the sheath for introduction into a side port of the hub, to which monitoring equipment is or can be attached, prior to placement of the sheath in the vessel and removal of the needle and dilator from the sheath. In such prior art assemblies blood flows from the vessel penetrated by the needle into either a syringe or a guidewire housing connected behind the sheath hub so long as the needle is in an advanced operative position. Consequently, with the needle in such an operative position, there is no blood flow communication with an interior cavity of the sheath hub or with a hub sideport. In the case of a guidewire housing connected behind the sheath hub, the housing must first be disconnected from the hub, assuming it can be disconnected, which is not always possible, in order to connect monitoring equipment at the rear of the hub. In such a case, unsanitary blood spillage is likely to occur. In the case of a syringe connected at the rear of the hub, the syringe must first be removed in order to connect monitoring equipment, again, with the likelihood of blood spillage. Even with more recently available blood containing, guidewire introducing syringes and bulbs, transducer tubing must be connected and, then, disconnected prior to guidewire advancement.

By means of our invention, these and other difficulties encountered using such prior art catheter assemblies are substantially eliminated.

SUMMARY OF THE INVENTION

It is an object of our invention to provide a catheter assembly having an introducer needle, fenestrated dilator and sheath which provides for communication of blood from a vessel being penetrated by the needle to a side port of the hub prior to insertion of the dilator and sheath into the blood vessel.

It is a further object of our invention to provide such a catheter assembly with provision for observing an early occurring blood flashback through a transparent or translucent body of a sheath and, in certain cases, through an underlying transparent or translucent dilator, near a distal end of the assembly, well within the field of vision of an operator who is concentrating on the region of needle penetration.

In accordance with these objects, we provide a catheter assembly which includes an elongated, hollow introducer needle adapted for insertion into a biological liquid containing region of a patient. A flexible, hollow tubular dilator defining at least one fenestration therein is also included, the dilator being adapted for slidable disposition over the needle. A flexible, hollow tubular sheath is provided which is adapted for slidable disposition over the dilator. The sheath includes at least one sideport which communicates with a lumen of the sheath. A means for conducting a biological liquid from the patient, as a result of insertion of the needle into the sideport through the first dilator fenestration is also provided.

These and other objects, features and advantages of the subject invention will become apparent to those skilled in the art from the following detailed description and attached drawings upon which, by way of example, only a preferred embodiment and certain other important embodiments of our invention are described and illustrated.

DESCRIPTION OF THE PREFERRED EMBODIMENT

Figure 1:
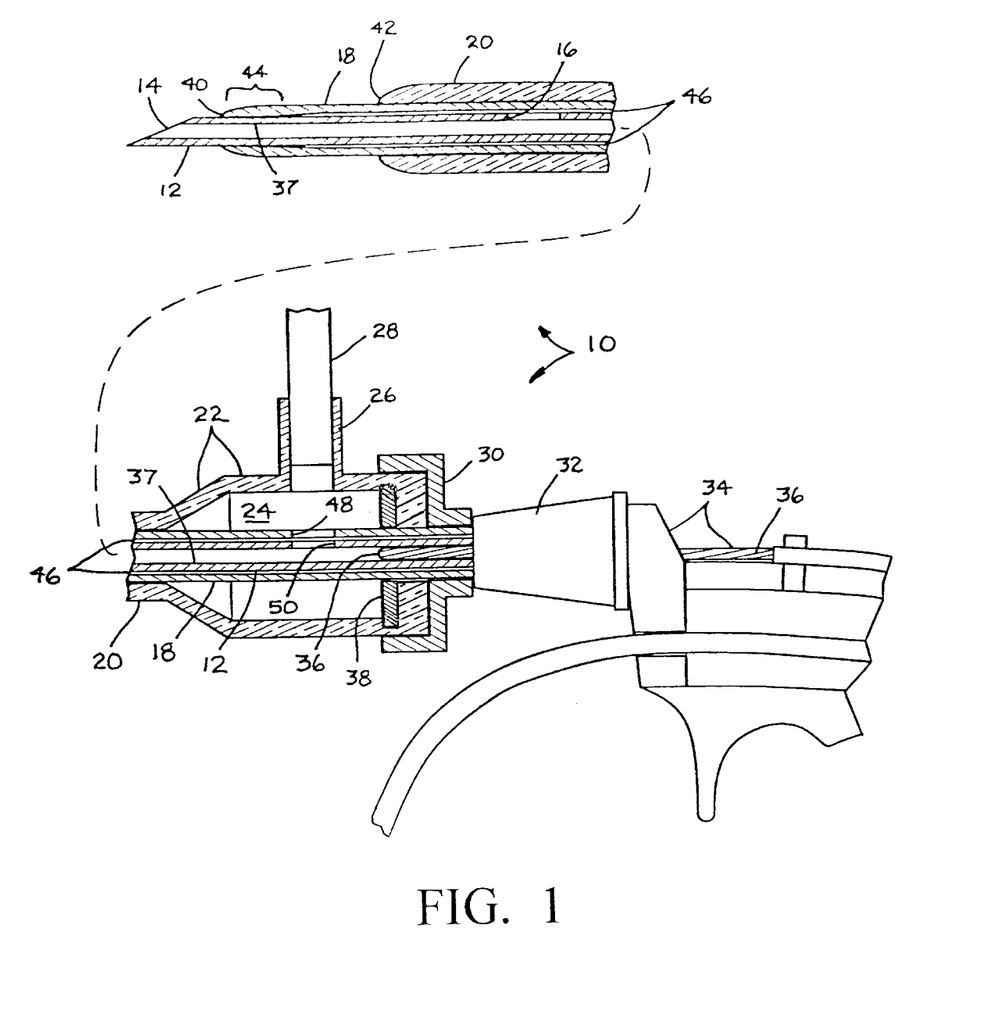
FIG. 1 shows a fragmented, longitudinal cross-section view of a catheter assembly, thus illustrating a preferred embodiment of our invention.

Referring now to the drawing figures and, in particular, to FIG. 1, there is shown, in a preferred embodiment of our invention, a catheter assembly, generally designated 10. The assembly 10 includes an elongated, flexible, hollow introducer needle 12 having a sharp, beveled, open ended tip 14 on a distal end thereof and a circular aperture or fenestration 16. The assembly 10 also includes an elongated, flexible, tubular dilator 18 slidably mounted over and around the needle 12 and an elongated, flexible, tubular sheath 20 slidably mounted over and around the dilator in close fitting relationship throughout its length. A hub 22 is attached to a proximal end of the sheath 20 and defines a generally cylindrically shaped interior chamber or cavity 24 therein and a hollow, cylindrically shaped sideport 26. The cavity 24 communicates both with the sheath 20, when the dilator 18 is removed, and with the sideport 26. A flexible, hollow tube 28, preferably being constructed of a transparent or translucent plastic, has one end portion which is frictionally fitted within the sideport 26. The tube 28 can be attached to conventional blood pressure monitoring equipment, a blood sampling device and/or liquid infusion equipment, all in the usual, well known manner.

The needle 12 extends through the sheath hub cavity 24 and through the center of a cap 30 which is attached over an otherwise open proximal end of the hub 22. A proximal end of the needle 12 is connected to a plastic needle hub 32 which, in turn, abuts a conventional guidewire assembly 34. The assembly 34 contains a guidewire 36 which may be advanced and retracted through the needle hub 32 and through a lumen 37 of the needle 12 to aid in placement of the needle as, for example, in a blood vessel, all in the usual, well known manner. The guidewire 36 is shown in a retracted position in FIG. 1. A conventional resilient diaphragm 38 is disposed in a proximal end portion of the hub cavity 24 through which the needle 12 and overlying dilator 18 extend. A proximal end portion of the dilator 18 is glued or otherwise affixed in and to a central collar of the cap 30. The diaphragm 38 thus seals the otherwise open proximal end of the hub cavity 24 around the dilator so that a biological liquid which may be present in the cavity 24 when the cap 30 is removed will not spill therefrom. A hole in the diaphragm 38 will resiliently close and seal in a liquid tight manner when the needle 12 and the dilator 18 are withdrawn therefrom.

FIG. 1 shows a distal end 40 the dilator 18 in its initial operative position closely spaced, proximally, from the distal end 14 of the needle 12. Also, in its initial operative position, a distal end 42 of the sheath 20 is closely space, proximally, from the dilator distal end 40. A distal end portion 44 of the dilator 18 closely fits around the needle 12 so as to prevent a biological liquid from entering the distal end 40 between the needle and dilator. But, proximal to the distal end portion 44, the dilator 18 is relatively loose fitting over the needle 12 to form a passageway 46 of annular cross-section between the needle and dilator which extends proximally from the distal end portion 44, across the needle fenestration 16 when the needle is in its advanced operative position as shown, and into the sheath hub cavity 24. A second fenestration 48 is also formed in the dilator 18 which is positioned within the cavity 24 and which communicates with the hub cavity and the sideport 26, external to the dilator and, with the passageway 46, between the dilator and needle. Both the dilator 18 and sheath 20 are preferably constructed of a transparent or translucent plastic material over at least a portion of the passageway 46 so as to permit visual recognition of blood or other biological liquid flow in the passageway 46. In typical operation, with the needle 12, dilator 18 and sheath 20 placed in their initial operative positions relative to one another as shown, and with conventional blood pressure monitoring equipment responsively connected to the tube 28, the needle is inserted into a biological organism with a view toward piercing an artery, for example. As the needle tip 14 enters a lumen of the artery, blood will flow under pressure, into the lumen 37 of the needle 12, thence proximally along the lumen to the fenestration 16, thence along both the needle lumen and, through the fenestration 16, into and along the passageway 46. Thereafter, the blood will flow out of the passageway 46 through the dilator fenestration 48 into the surrounding hub chamber 24 and through the sideport 26 into the tube 28. Conventional blood pressure monitoring of the blood in the tube 28 will show with certainty that the needle 12 has, indeed pierced the artery as desired.

The conventional guidewire assembly 34 can then be used to advance the guidewire 36 through and beyond the distal end 14 of the needle 12 to assure that the guidewire encounters no resistance and is, indeed, advancing along the lumen of the artery from the point of needle puncture.

A major advantage offered by our catheter assembly 10 of the present example is that blood pressure monitoring can be observed immediately upon insertion of the needle 12 into an artery lumen before the dilator 18 and sheath 20 are advanced over the needle into the artery to assure a proper needle insertion without having to first dismantle parts of the assembly in order to connect blood pressure monitoring equipment. No other catheter assemblies having a dilator and sheath are known to have such a desirable feature. Moreover, not only will pulsatile arterial, blood flow immediately be noted in the tubing 28 and associated monitor upon needle puncture of the artery, blood flow in the passageway 46 can be immediately noted by the user due to a substantial darkening of the transparent or translucent materials of the dilator 18 and sheath 20 over the passageway 46. This is particularly advantageous since a distal end portion of the sheath 20 and underlying portion of the dilator 18 over a distal end portion of the passageway 46 will be located near the position of insertion of the needle 12 into a patient, well within the field of vision of the operator who, at the time of insertion of the needle, will be closely focused on the area of needle penetration.

As an option, the needle 12 may also have a second fenestration 50 which registers with the dilator fenestration 48 in the hub cavity 24 to permit blood or other biological liquid to flow from a patient through the lumen of the needle directly into the cavity 24, sideport 26 and tube 28. If desired, this may be the only route provided for such liquid flow to the hub cavity and sideport 26, whereby the needle fenestration 16 and passageway 46 will not be required and, in that event, the dilator 18 may closely fit over the needle 12 for its entire length. Also, in that event, the dilator 18 and sheath 20 need not be constructed of a transparent or translucent material. While this option also provides for immediate monitoring of blood pressure upon injection of the needle 12 into a blood vessel, for example, without the need to disconnect portions of the catheter assembly 10, the trade off will be the loss of means for observing blood flow in the now, non-existent passageway 46 near the distal end of the assembly and near the point of puncture of the patient.

Figure 2:
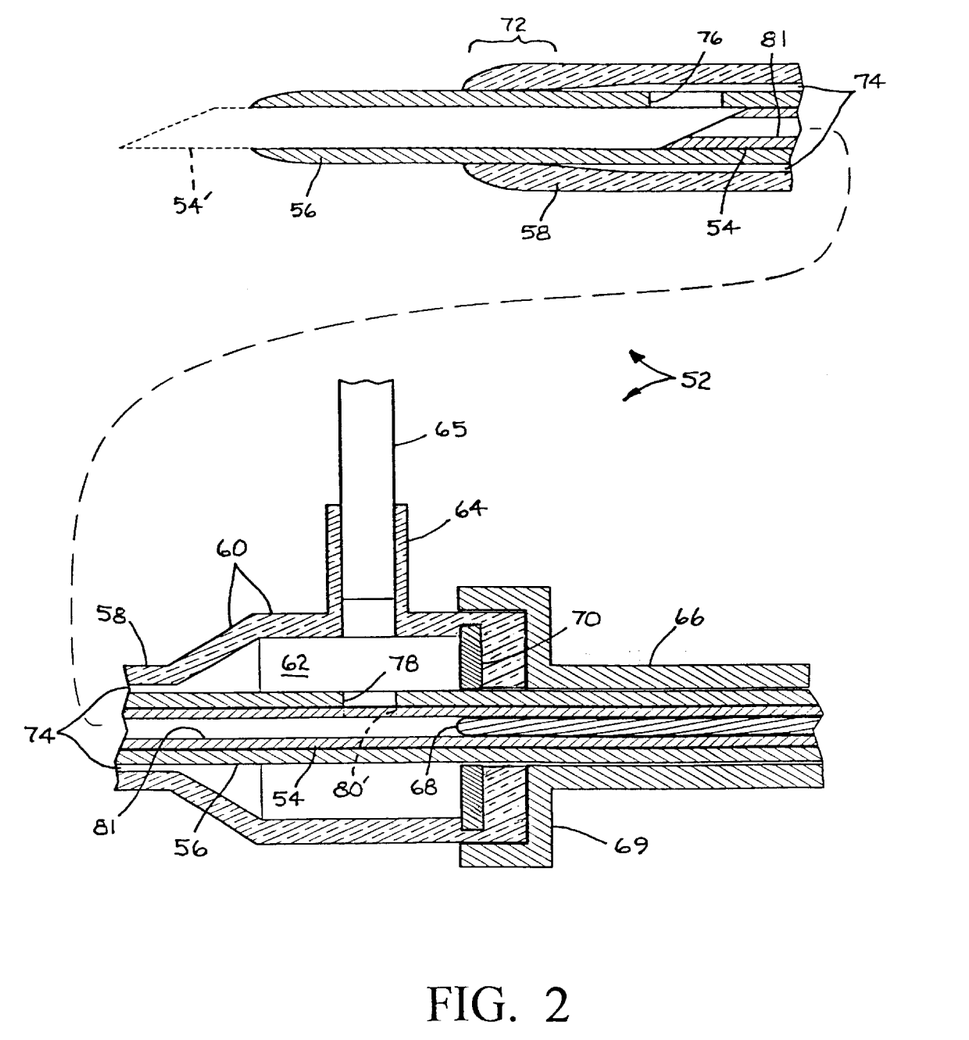
FIG. 2 shows a fragmented, longitudinal cross-section view of a catheter assembly, thus illustrating another important embodiment of our invention.

Referring now to FIG. 2, there is shown, in another important embodiment of our invention, a catheter assembly generally designated 52, including a hollow introducer needle 54, a flexible tubular dilator 56 slidably mounted over the needle in close fitting relationship throughout their common lengths, and a flexible tubular sheath 58 slidably mounted over the dilator and connected on a proximal end thereof to a hub 60. As in the previous example, the hub 60 defines an interior chamber or cavity 62 and includes a sideport 64 communicating with the cavity. A flexible plastic tube 65 is shown with one end portion being frictionally inserted in the sideport 64. In this example, a conventional needle and guidewire housing 66 for a retractable needle and retractable guidewire 68 is shown which is connected by means of a cap 69 to an otherwise open proximal end of the hub 60. A conventional diaphragm 70 is disposed in a proximal end portion of the hub cavity 62 around the dilator 56 to provide a substantially liquid tight seal at the proximal end of the cavity around the dilator to prevent a liquid from spilling out of the cavity upon removal of the housing 66 and cap 69 from the hub 60. A hole formed through the diaphragm 70 will resiliently close to form a liquid tight seal upon withdrawal of the dilator, needle and guidewire therefrom.

The needle 54 is shown, in full, in a partially retracted position within the dilator 56 and, in phantom, at 54', in a fully advanced initial operative position relative to the dilator and sheath 58. The sheath 58 contains a distal end portion 72 which closely fits on and around the dilator 56 in a slidable, yet liquid tight manner, to prevent a biological liquid from entering the distal end of the sheath between the latter and the dilator. But, immediately proximal to the close fitting distal end portion 72 and extending proximally to the hub 60, the sheath 58 is loosely fitted on the and around the dilator 56 to form a passageway 74 of annular cross-section between the dilator and sheath. The passageway 74 thus communicates with the cavity 62 around the dilator 56 and, through the cavity, with the sideport 64 and tube 65. The dilator 56 includes a first circular fenestration 76 therein which opens into a distal end portion of the passageway 74 when the dilator and sheath 58 are disposed in their initial operative positions relative to one another as shown.

The dilator 56 also defines a second circular fenestration 78 within the hub cavity 62, preferably in registry with the sideport 64. The needle 54 also contains a circular fenestration 80' which registers with the second dilator fenestration 78 when the needle is in its advanced operative position 54' as shown in the phantom in FIG. 2. When the needle 54 is partially retracted, as shown in full in FIG. 2, the fenestration represented by 80' would be located somewhere within the housing 66, to the right of its present position as viewed.

In typical operation, the needle 54 is advanced to its initial operative position as shown at 54' and conventional blood pressure monitoring and/or other equipment is connected to the tube 65. The guidewire 68 is placed in a retracted position as shown. Under such initial conditions, the fenestration 78 and 80' register with one another. The needle 54' is inserted into a patient and into a blood vessel. Upon proper placement of the needle 54' in an artery, for example, blood will flow, under pressure, from the artery through a lumen 81 of the needle, thence through the registered needle and dilator fenestrations 80' and 78, respectively, into the surrounding hub chamber 62 and finally, into the sideport 64 and tube 65. Provided the tube 65 is either transparent or translucent, an immediate indication of an arterial puncture will be noted therein. Thus, the transparent or translucent tube 65 forms a means for viewing the presence of a liquid flowing through the needle and dilator fenestrations 80' and 78, respectively, from a biological liquid containing region of a patient by way of a lumen in the needle 27. The monitor will confirm the presence of a pulsatile arterial blood flow. Thereafter, the dilator 56 and sheath 58 may be slid forwardly, to the left as viewed, over the needle 54, 54' such that the dilator enters the artery lumen first, followed by the sheath 58. The needle 54 and guidewire 68 are then retracted such that, when the needle passes the first dilator fenestration 76, blood will flow under pressure, from the artery into the lumen of the dilator 56, thence through the first fenestration into and along the passageway 74 and into the hub chamber 62, sideport 64 and tube 65. Thus, by means of this embodiment of our invention, proper insertion of the dilator 56 into the artery can be immediately observed on monitoring equipment attached to the tube 65 without the necessity of disconnecting portions of the catheter assembly 52 in order to connect such monitoring equipment. Also, provided the sheath 58 or at least a portion thereof which overlies the passageway 74, is made of a transparent or translucent material, an immediate blood flashback through the passageway 74 distal to the hub 60 will be visually observed.

Figure 3:
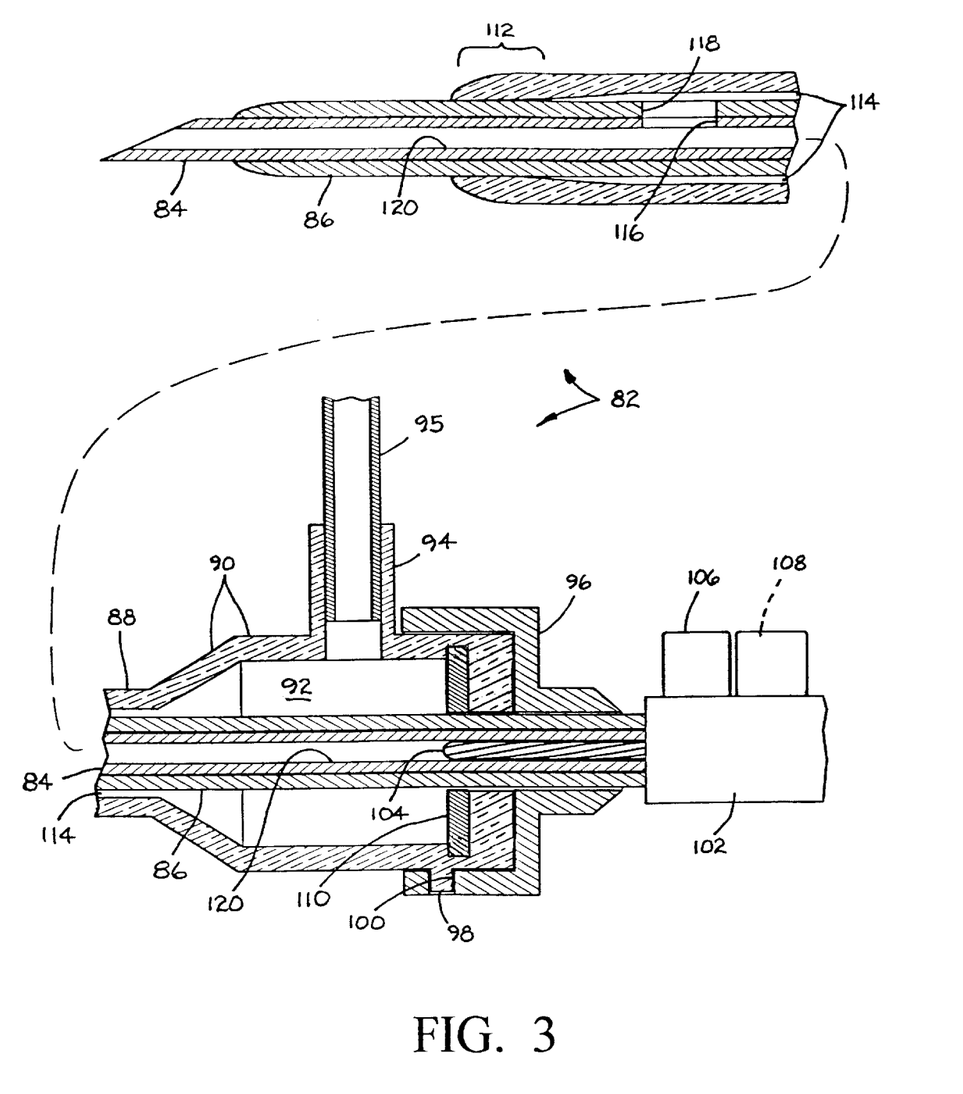
FIG. 3 shows a fragmented, longitudinal cross-section view of a catheter assembly, thus illustrating yet another important embodiment of our invention.

Referring now to FIG. 3, there is shown, in another important embodiment of our invention, a catheter assembly, generally designated 82, which includes a retractable hollow introducer needle 84, a flexible dilator 86 slidably mounted over the needle in close fitting relationship, and a flexible sheath 88 slidably mounted over the dilator and attached on a proximal end to a sheath hub 90. The hub 90 defines a generally cylindrically shaped internal cavity 92 and contains a sideport 94 which communicates with the cavity. A flexible plastic tube 95 frictionally fits in the sideport 94. A conventional end cap 96 covers an otherwise open proximal end of the cavity 92 and latches to the hub 90 by means of a tab 98 on the hub and a keyway 100 in the cap, all in a usual and well known manner. A conventional needle and guidewire assembly 102 contains both the needle 84 and a guidewire 104 when in their fully retracted positions.

In FIG. 3 the needle 84 is shown in a fully advanced initial operative position and the guidewire 104 is shown in a fully retracted position. A finger tab 106, shown in a fully advanced position on the housing 102, controls advancement and retraction of the needle 84. A similar finger tab 108, shown in phantom in a fully advanced position, controls advancement and retraction of the guidewire 104. However, since the guidewire 104 is shown in retracted position in the drawing figure, the finger tab 108, as shown in phantom, would in actuality, be located on the housing 102 well to this right of its phantom position as viewed, off the drawing. The finger tabs 106 and 108 are slidable along an elongated slot in the housing 102 and connect through the slot to the needle 84 and guidewire 104, respectively. As in the previous examples, a resilient diaphragm 110 is lodged in a proximal end portion of the hub cavity 92 to provide a leak proof seal of the otherwise open proximal end of the hub 90 to prevent a liquid spillage from the chamber 92 around the dilator 86 when the cap 96 is removed.

The sheath 88 includes a distal end portion 112 which closely fits, slidably, over and around the dilator 86. A remaining portion of the sheath 88, proximal to the distal end portion 112, loosely fits over and around the dilator 86 to form a passageway 114 of annular cross-section between the sheath and dilator, which passageway communicates with the hub cavity 92, sideport 94, and tube 95. In the present example of our invention, the needle 84 defines a fenestration 116 which, in its fully advanced initial operative position as shown, registers with a fenestration 118 formed in the dilator 86. When the needle 84, dilator 86 and sheath 88 are disposed in their initial operative positions relative to one another, as shown, the fenestrations 116, 118 provide communication between a lumen 120 of the needle and a distal end portion of the passageway 114, proximal to the sheath distal end portion 112. The sheath 88 or, at least a portion thereof which surrounds the passageway 114, is preferably made of a transparent or translucent plastic such that it will darken or otherwise show the presence of a biological liquid in the passageway, or a portion thereof, which is introduced therein from a patient through the needle lumen 120 and registered fenestrations 116, 118.

Thus, an initial blood or other biological liquid flashback will be observed in the passageway 114 through the sheath 88 immediately upon proper placement of the needle 84. Such a flashback will also be observed in tubing 95, assuming it to be made of a transparent or translucent material and, of course, blood pressure monitoring equipment and/or blood sampling devices can be attached to the tube 95 as desired. Accordingly, recognition of proper placement of needle 84 can be had prior to insertion of the dilator 86 into a patient without need for changing connections on the assembly 82. Also, even after the dilator 86 and sheath 88 have been moved, distally over the needle 84 so that the dilator enters the patient and as the needle 84 is withdrawn past the fenestration 118, proper placement of the dilator can be recognized by biological liquid flow from the patient through the dilator and dilator fenestration into the passageway 114, cavity 92, sideport 94, and tube 95.

Figure 4:
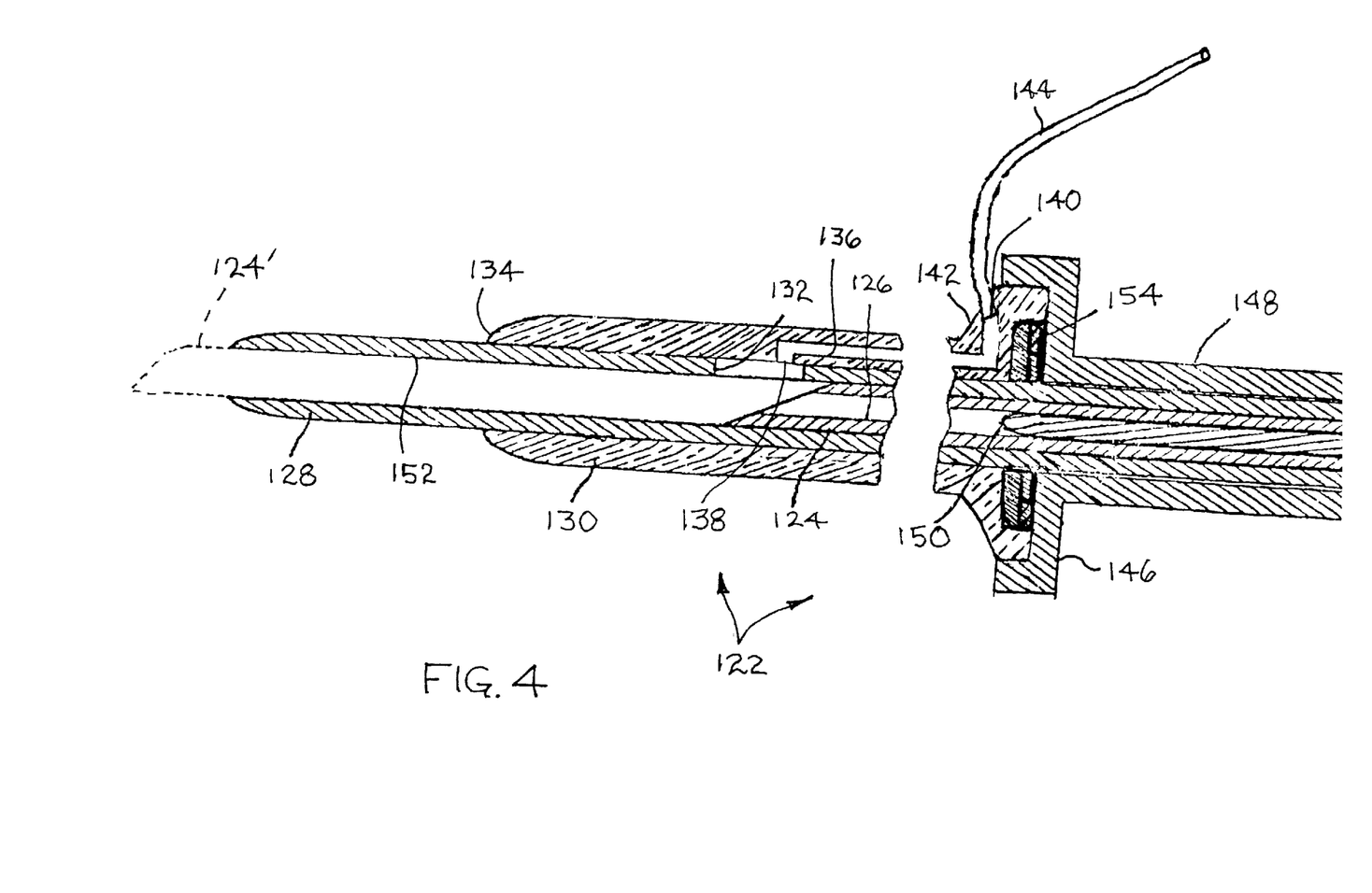
FIG. 4 shows a fragmented, longitudinal cross-section view of a catheter assembly, thus illustrating still another important embodiment of our invention.

Referring now to FIG. 4 there is shown, in another important embodiment of our invention, a catheter assembly generally designated 122. The assembly 122 includes a hollow introducer needle 124 having a lumen 126, a flexible hollow dilator 128 slidably disposed over the needle and a flexible hollow sheath 130 slidably disposed over the dilator. The needle 124 is shown in full in a partially retracted position and in phantom at 124' at its fully advanced operative position relative to the dilator 128 and sheath 130. The dilator 128 defines a fenestration 132 which is proximally spaced from a distal end 134 of the sheath 130 when the dilator and sheath are located in their operative positions relative to one another for insertion over the needle 124' into a patient. A hollow tubular passageway 136 is formed within the material forming the sheath 130 which extends distally, from an end 138 which communicates with the fenestration 132 when the dilator 128 and sheath are in their operative positions relative to one another, to a port 140 located on a sheath hub 142. A flexible, hollow plastic line 144 is frictionally inserted or glued into the port 140 which can be connected to blood pressure monitoring equipment, blood sampling equipment and/or drug infusion devices, all in the usual and well known manner.

In this example, the sheath hub 142 does not define a cavity surrounding the dilator 128 and needle 124, but merely provides a port for a proximal end of the passageway 136 and a mass over which a cap 146 of a conventional housing 148 for a retractable needle and guidewire 150 can be secured in a suitable and well known manner. The assembly 122 thus permits communication between a lumen 152 of the dilator 128 and the port 140, through the dilator fenestration 132 and passageway 136 as soon as the needle 124' has made the proper puncture, the dilator 128 has been advanced and the needle has been withdrawn proximally through the dilator lumen 152 to the position shown at 124. Here, again, blood pressure monitoring can be made, blood samples can be taken and various drugs can be infused into a patient through the line 144, passageway 136, and dilator lumen 152 without the necessity of altering connections to the hub 142. A conventional flexible, resilient diaphragm 154 is inserted in an open ended slot formed in a proximal end portion of the hub 142 through which the needle 124 and dilator 128 extend. The diaphragm 154 is of the type which will resiliently seal itself upon withdrawal of the dilator 128 and needle 124 therefrom as for example, when the cap 146 and housing 148 are removed from the hub 142.

Although the present invention has been described with respect to specific details of a preferred embodiment of the invention and certain other important embodiments thereof, it is not intended that such details limit the scope and coverage of this patent other than as specifically set forth in the following claims.

We claim:

1. A catheter assembly comprising:
    an elongated hollow introducer needle adapted for insertion into a biological liquid containing region of a patient;
    a flexible, hollow tubular dilator for forming a first stage dilation of an access opening in a patient, said dilator having a main lumen in which said needle is removably and operatively slidably disposed, said dilator defining a first dilator fenestration through a side wall thereof;
    a flexible, hollow tubular sheath having a main lumen in which said dilator is removably and operatively, slidably disposed for forming a second stage dilation of the access opening in the patient which is larger than said first stage dilation, said sheath including at least one sideport which communicates with the main lumen of said sheath, and
    means for conducting a biological liquid from said patient, as a result of insertion of said needle into said region, into said sideport through said first dilator fenestration said sideport communicating with the main lumen of said dilator at least under circumstances wherein said needle is retracted proximally beyond said first dilator fenestration.

2. The catheter assembly of claim 1 wherein said sheath further includes a hub defining an internal cavity therein which communicates with said sheath lumen at least when said sheath is not disposed over said dilator, said dilator being adapted to extend through said sheath into said cavity, said sideport being attached to said hub for communication with said cavity external to said dilator.

3. The catheter assembly of claim 1 wherein said sheath includes a hub formed on a proximal end portion thereof, said conducting means comprising a passageway formed within a sidewall of said sheath which extends from a first opening in said sheath lumen on a distal end thereof into said hub to a second opening on a proximal end thereof on a surface of said hub to form a sideport, the first opening communicating with said first dilator fenestration when said dilator and sheath are disposed in operative positions relative to one another for commencement of insertion of said needle, dilator and sheath into said region.

4. The catheter assembly of claim 2 wherein said conducting means comprises a passageway formed between lengthwise portions of said needle and dilator, a distal end of said passageway being proximally spaced from a distal end of said dilator, said needle containing a needle fenestration for conducting said liquid from a lumen of said needle into a distal end portion of said passageway at a position which is distally spaced from said hub when said needle and dilator are disposed in initial operative positions relative to each another for commencement of insertion of said needle into said region, said first dilator fenestration being located within said cavity for conducting said liquid from said passageway into said cavity and sideport, said passageway extending between and being in communication with said needle fenestration and said first dilator fenestration.

5. The catheter assembly of claim 2 wherein said conducting means comprises a passageway formed between lengthwise portions of said dilator and sheath which extends between a position which is proximally spaced from a distal end of said sheath and said hub cavity when said dilator and sheath are disposed in initial operative positions relative to each other for commencement of insertion of said needle into said region, said first dilator fenestration being positioned in communication with a distal end portion of said passageway which is distally spaced from said hub for introducing said liquid from said region through said dilator into said passageway upon insertion of said dilator into said region and upon withdrawal of said needle proximally through said dilator past said first dilator fenestration, a proximal end of said passageway communicating with said cavity for introduction of said liquid from said passageway into said cavity and sideport.

6. The catheter assembly of claim 2 wherein said conducting means comprises a passageway formed between lengthwise portions of said dilator and sheath which extends from a position which is proximally spaced from a distal end of said sheath into said cavity when said dilator and sheath are disposed in initial operative positions relative to each other for commencement of insertion of said needle into said region, said first dilator fenestration being located so as to communicate with a distal end portion of said passageway and which is distally spaced from said hub when said dilator and sheath are disposed in said initial operative positions, said needle containing a needle fenestration which communicates with said first dilator fenestration when said needle, dilator and sheath are disposed in said operative positions such that, when said needle is inserted into said region, said liquid can flow into a lumen of said needle, thence through said needle fenestration and said first dilator fenestration into and through said passageway and into said cavity and sideport.

7. The catheter assembly of claim 4 wherein said needle contains a second fenestration located within said cavity in registry with said first dilator fenestration when said needle, dilator and sheath are disposed in initial operative positions relative to one another for commencement of insertion of said needle into said region, whereby said liquid can flow from said region, through a lumen of said needle, thence through said second needle fenestration and first dilator fenestration into said cavity and sideport.

8. The catheter assembly of claim 4 wherein at least a portion of the length of said dilator which overlies said passageway and at least a portion of the length of said sheath which overlies said portion of said dilator when said dilator and sheath are disposed in said initial operative positions are constructed of a material which will permit visual recognition of the presence of said liquid in said passageway external to said hub.

9. The catheter assembly of claim 4 further comprising a resilient diaphragm disposed in a proximal end portion of said sheath hub for sealing a proximal end portion of said cavity in a liquid tight manner.

10. The catheter assembly of claim 5 wherein at least a portion of the length of said sheath which overlies said passageway external to said hub when said dilator and sheath are disposed in said initial operative positions is constructed of a material which will permit visual recognition of the presence of said liquid in said passageway external to said hub.

11. The catheter assembly of claim 5 further comprising a first needle fenestration formed in said needle for disposition in registry with a second dilator fenestration within said cavity when said needle, dilator and sheath are disposed in said initial operative positions relative to each other.

12. The catheter assembly of claim 5 further comprising a resilient diaphragm disposed in a proximal end portion of said sheath hub for sealing a proximal end portion of said cavity in a liquid tight manner.

13. The catheter assembly of claim 6 further comprising a resilient diaphragm disposed in a proximal end portion of said sheath hub for sealing a proximal end portion of said cavity in a liquid tight manner.

14. A catheter assembly comprising:
an elongated, hollow introducer needle having a sharp tip on a distal end for insertion into a liquid containing region of a biological organism;
an elongated, hollow, flexible tubular dilator having a main lumen in which said needle is operatively and removably slidably disposed, said dilator being adapted to form a first stage dilation of an access opening in a patient, said dilator defining at least one fenestration through a sidewall thereof which is spaced proximally from an open distal end of said dilator;
an elongated, hollow flexible tubular sheath having a main lumen in which said dilator is operatively and removably slidably disposed for forming a second stage dilation of the access opening in the patient which is larger than said first stage dilation, an open distal end of said sheath being proximally spaced from said distal end of said dilator when said dilator and sheath are disposed in position for insertion into said organism, a distal end portion of said sheath being in close fitting, liquid tight relationship with said dilator, a portion of said sheath extending proximally from said sheath distal end portion having an inside diameter which is greater than an outside diameter of said dilator to form a passageway between said dilator and sheath, said at least one fenestration being located so as to open into a distal end portion of said passageway when said dilator and sheath are operatively disposed on said needle for commencement of said insertion such that a biological liquid can flow into a distal end of said dilator, thence through said fenestration and into and along said passageway as said dilator enters a liquid containing region of said organism, and as said needle is withdrawn proximally from said region through said dilator and proximally past said fenestration.

15. A catheter assembly comprising:
an elongated, hollow, introducer needle defining a fenestration which is proximally spaced from a distal end thereof;
an elongated, hollow, flexible tubular dilator removably, slidably disposed over said needle, said dilator defining a fenestration which is proximally spaced from a distal end of said dilator, said dilator distal end being proximally spaced from said needle distal end when said dilator is operatively positioned over said needle for commencement of an insertion of said needle and dilator into a liquid containing region of a biological organism such that said needle fenestration communicates with said dilator fenestration;
an elongated, hollow, flexible tubular sheath removably slidably disposed over said dilator, a distal end of said sheath being proximally spaced from said dilator distal end when said sheath is operatively positioned over said dilator for commencement of an insertion of said needle, dilator and sheath into said region, such that a distal end portion of said sheath, extending from said sheath distal end to a position distally spaced from said dilator fenestration, fits over said dilator in a liquid tight manner; and
means for viewing the presence of a liquid flowing through said needle and dilator fenestrations from said region by way of a lumen in said needle.

16. The assembly of claim 15 wherein said viewing means comprises at least a portion of a remaining length of said sheath extending proximally from said sheath distal end portion being loosely fitting over said dilator to form a passageway for a biological liquid between said sheath and dilator, which passageway communicates with said needle and dilator fenestrations, said portion of said remaining length of said sheath comprising a translucent material for darkening in response to the flow of said liquid in said passageway.

17. The assembly of claim 16 wherein said viewing means comprises at least a portion of a remaining length of said sheath extending proximally from said sheath distal end portion being loosely fitting over said dilator to form a passageway for a biological liquid between said sheath and dilator, which passageway communicates with said needle and dilator fenestrations, said portion of said remaining length of said sheath comprising a transparent material for permitting the viewing of said liquid flowing in said passageway.

* * * * *

UNITED STATES PATENT AND TRADEMARK OFFICE
CERTIFICATE OF CORRECTION

| | | |
|---|---|---|
| PATENT NO. | : 6,726,659 B1 | Page 1 of 1 |
| APPLICATION NO. | : 09/457661 | |
| DATED | : April 27, 2004 | |
| INVENTOR(S) | : John E. Stocking and Francis Duque | |

It is certified that error appears in the above-identified patent and that said Letters Patent is hereby corrected as shown below:

In Claim 17, at column 11, line 1, please delete "claim 16" and insert --claim 15--.

Signed and Sealed this

Eighteenth Day of November, 2008

JON W. DUDAS
*Director of the United States Patent and Trademark Office*